US 8,090,177 B2

(12) United States Patent
Venkataraman et al.

(10) Patent No.: US 8,090,177 B2
(45) Date of Patent: Jan. 3, 2012

(54) METHODS FOR DETECTION AND CHARACTERIZATION OF ATYPICAL VESSELS IN CERVICAL IMAGERY

(75) Inventors: Sankar Venkataraman, Honolulu, HI (US); Wenjing Li, Honolulu, HI (US); Ulf Peter Gustafsson, Honolulu, HI (US)

(73) Assignee: STI Medical Systems, LLC, LaJolla, CA (US)

( * ) Notice: Subject to any disclaimer, the term of this patent is extended or adjusted under 35 U.S.C. 154(b) by 824 days.

(21) Appl. No.: 12/221,328

(22) Filed: Aug. 1, 2008

(65) Prior Publication Data

US 2010/0027863 A1 Feb. 4, 2010

(51) Int. Cl.
*G06K 9/00* (2006.01)

(52) U.S. Cl. ........ 382/130; 382/131; 382/134; 382/128; 382/173; 382/199; 382/205; 382/224; 382/260; 382/266; 382/275; 600/160; 600/109

(58) Field of Classification Search .................. 382/130, 382/131, 134, 128, 173, 199, 205, 224, 260, 382/266, 275; 600/160, 109
See application file for complete search history.

(56) References Cited

U.S. PATENT DOCUMENTS

| | | | | |
|---|---|---|---|---|
| 5,257,182 A * | 10/1993 | Luck et al. | ..................... | 382/224 |
| 5,462,059 A | 10/1995 | Ferrara et al. | | |
| 5,832,111 A * | 11/1998 | Florent | ......................... | 382/171 |
| 6,135,965 A | 10/2000 | Tumer et al. | | |
| 6,221,623 B1 | 4/2001 | Smith-McCune et al. | | |
| 6,236,886 B1 | 5/2001 | Cherepenin et al. | | |
| 6,351,663 B1 | 2/2002 | Flower et al. | | |
| 7,074,188 B2 | 7/2006 | Nair et al. | | |
| 2004/0086162 A1 * | 5/2004 | Doi et al. | ..................... | 382/131 |
| 2006/0002631 A1 * | 1/2006 | Fu et al. | ........................ | 382/294 |
| 2006/0002632 A1 * | 1/2006 | Fu et al. | ........................ | 382/294 |
| 2006/0257031 A1 | 11/2006 | Abramoff et al. | | |
| 2006/0291710 A1 * | 12/2006 | Wang et al. | ..................... | 382/131 |
| 2007/0019846 A1 | 1/2007 | Bullitt et al. | | |
| 2007/0287897 A1 | 12/2007 | Faris | | |
| 2008/0159604 A1 | 7/2008 | Wang et al. | | |

OTHER PUBLICATIONS

Pogue, Brian W. et al., "Image analysis for discrimination of cervical neoplasia," Journal of Biomedical Optics, vol. 5, No. 1, 72-82 (Jan. 2000).
Ji, Qiang et al., "Texture analysis for classification of cervix lesions," IEEE Trans. Med. Imag. vol. 19, No. 11, 1144-1149 (Nov. 2000).
Ji, Qiang et al., "Classifying cervix tissue patterns with texture analysis," Pattern Recognition, vol. 33, 1561-1573 (2000).
Srinivasan, Yeshwanth et al.,"A probabilistic approach to segmentation and classification of neoplasia . . . ," Proc. SPIE, vol. 5747, 995-1003 (2005).
Li, Wenjing et al., "Detection and characterization of abnormal vascular patterns . . . ," LNCS—Advances in Visual Computing, vol. 4292, 1543-1552 (2006).

* cited by examiner

*Primary Examiner* — Wesley Tucker
*Assistant Examiner* — Mark Roz
(74) *Attorney, Agent, or Firm* — Martin E. Hsia

(57) ABSTRACT

The present invention discloses a method for the detection of atypical vessels in digital cervical imagery. A pre-processing stage is applied to enhance the contrast of blood vessel features compared to the surrounding tissue. Next, a segmentation stage is applied to identify regions of interest for atypical vessels using texture and gradient information. Finally, a post-processing stage (1) identifies other clinically relevant features in the cervical imager, and removes these features from the region of interest; and (2) uses color, size, and shape information to further refine the region of interest to eliminate false positives and determine a final region of interest. This automated method of atypical vessel detection is especially useful for diagnostic purposes such as cervical cancer detection.

1 Claim, 9 Drawing Sheets

METHODS FOR DETECTION AND CHARACTERIZATION OF ATYPICAL VESSELS IN CERVICAL IMAGERY

TECHNICAL FIELD

This invention relates to medical imaging and, more specifically, to the computer aided detection and diagnosis of uterine cervical cancer and pre-cancerous lesions. The invention provides an automated method to detect atypical blood vessels in cervical imagery for the diagnosis of cancer.

BACKGROUND ART

Although this invention is being disclosed in connection with cervical cancer, it is applicable to many other areas of medicine. Uterine cervical cancer is the second most common cancer in women worldwide, with nearly 500,000 new cases and over 270,000 deaths annually (IARC, "Globocan 2002 database," International agency for research in cancer, 2002, incorporated herein by reference). Because invasive disease is preceded by pre-malignant Cervical Intraepithelial Neoplasia (CIN), if detected early and treated adequately, cervical cancer can be universally prevented (D. G. Ferris, J. T. Cox, D. M. O'Connor, V. C. Wright, and J. Foerster, *Modern Colposcopy. Textbook and Atlas*, pp. 1-699, American Society for Colposcopy and Cervical Pathology, 2004, incorporated herein by reference). Colposcopy is the primary diagnostic method in the United States to detect CIN and cancer following an abnormal cytological screen (Papanicolaou or "pap" smear). The purpose of a colposcopic examination is to identify and rank the severity of lesions, so that biopsies representing the highest-grade abnormality can be taken, if necessary. Pre-cursor lesions of cervical cancer and invasive cancer exhibit certain distinctly abnormal morphological (relating to form and structure) features that can be identified during the colposcopic examination (A. Stafl, R. F. Mattingly, Colposcopic diagnosis of cervical neoplasia, *Obstet. Gynecol* 168-76 (1973), incorporated herein by reference; M. Coppelson, J. C. Dalrymple, K. H. Atkinson, Colposcopic differentiation of abnormalities arising in the transformation zone, *Contemp Colposcopy*, 83-110 (1993), incorporated herein by reference; R. Reid, E. P. Krums, B. R. Herschman, et al., Genital warts and cervical cancer V: The tissue basis of colposcopic change, *Am. J Obstet. Gynecol*, 293-303 (1984), incorporated herein by reference; J. L. Benedet, G. H. Anderson, D. A. Boyes, Colposcopic diagnosis of invasive and occult carcinoma of the cervix, *Obstet. Gynecol.*, 557-562 (1985), incorporated herein by reference).

Among the colposcopic signs that identify pre-cancerous regions are abnormal vascular patterns called punctation and mosaic. Atypical vessels are major diagnostic features (R. Reid, E. P. Krums, B. R. Herschman, et al., Genital warts and cervical cancer V: The tissue basis of colposcopic change, *Am. J. Obstet. Gynecol.*, 293-303 (1984), incorporated herein by reference; R. Reid and P. Scalzi, Genital warts and cervical cancer VII: An improved colposcopic index for differentiating benign papillomaviral infections from high-grade cervical intraepithelial neoplasia, *Am. J Obstet. Gynecol.* 153(6): 611-618. 1985, incorporated herein by reference). As such, automated methods to detect and characterize abnormal vascular patterns in digital cervical imagery are desirable to assist the physician during the diagnostic process. Accounts of semi-automatic analysis of cervical vascular patterns have been presented by Ji et al. (Q. Ji, J. Engel, and E. Craine, Classifying cervix tissue patterns with texture analysis, *Pattern Recognition* 33, 1561-1573 (2000), incorporated herein by reference; Q. Ji, J. Engel, and E. Craine, Texture analysis for classification of cervix lesions, *IEEE Trans. Med. Imag.* 19, 1144-1149 (2000), incorporated herein by reference). Results on detecting mosaic patterns using color and geometric features have been reported by Srinivasan et al. (Y. Srinivasan, D. Hernes, B. Tulpule, S. Yang, J. Guo, S. Mitra, et al., A probabilistic approach to segmentation and classification of neoplasia in uterine cervix images using color and geometric features, *Proc. of SPIE* 5747, 995-1003, (2005), incorporated herein by reference). A fully automated approach for the detection and characterization of punctation and mosaic has been presented by Li et al. (W. Li and A. Poirson, Detection and characterization of abnormal vascular patterns in automated cervical image analysis, Lecture Notes in *Computer Science—Advances in Visual Computing* 4292, 627-636 (2006), incorporated herein by reference).

Atypical blood vessels are superficial vessels that exhibit bizarre variations in diameter, course, spacing, and branching patterns, when compared with normal blood vessels. A schematic of atypical blood vessels is presented in FIG. 1. The atypical vessels are generally very dilated in comparison with other typical capillaries seen on the cervix. Atypical blood vessels traverse superficially (near to the surface or just under the skin) within the epithelium, often oriented parallel to the surface. Although normal variants may be seen, atypical vessels are most commonly associated with invasive cancer (D. G. Ferris, J. T. Cox, D. M. O'Connor, V. C. Wright, and J. Foerster, *Modern Colposcopy. Textbook and Atlas*, pp. 1-699, American Society for Colposcopy and Cervical Pathology, 2004, incorporated herein by reference).

Blood vessels in benign epithelia (normal tissue) branch in a tree-like fashion with wide trunks gradually giving rise to both large and small branches. However, atypical vessels may display an abrupt change in diameter or irregularly varying caliber (diameter). These vessels also exhibit random directionality, changing their direction suddenly. Moreover, atypical vessels are superficially positioned and covered by very few layers of epithelium. Compared to regular vessel patterns, the intercapillary distances are greater in atypical vessels. Early signs of cancer may be demonstrated by normal, to slightly increased, vessel spacing. In invasive cancer, most capillaries are spaced about 300 μm (micrometers or millionths of a meter) apart and, as the stage of invasive cancer increases, the percentage of atypical vessels with intercapillary distances greater than 450 μm increases proportionally. In addition, atypical vessels are distributed randomly or non-uniformly. The number of atypical blood vessels increases as the severity of cancer increases. In early stage cancers, only a few atypical vessels can typically be seen. Atypical vessels are rare in dysplasia (<0.7%), but more common in CIN3 (3% to 17%) and early invasion (44% to 77%). Atypical vessels become most common in invasive cancer (84% to 97%). Atypical blood vessels associated with cancer have been described and categorized subjectively as resembling corkscrews, tadpoles, hairpins, spaghetti, and other unusual configurations. The atypical blood vessels of adenocarcinoma, a cancer originating in the glandular tissue, have been described as resembling tendrils, roots, willow branches, and waste threads. They may arise from alterations of central loop capillaries within the columnar epithelium lining the uterus.

The present invention presents a systematic framework that automatically detects and characterizes atypical vessels in digital cervical imagery. The following patents and patent applications may be considered relevant to the field of the invention:

U.S. Patent Application Publication No. 2008/0159604 to Wang, Allan et al., incorporated herein by reference, discloses an apparatus and method for determining an extent of vascularization in which (i) a digital representation of blood vessels in a selected area is generated; (ii) one or more statistical quantitative measures for the blood vessels in the selected area are calculated; and (iii) the one or more statistical quantitative measures are compared to corresponding statistical standards to determine an extent of vascularization. The statistical quantative measures may include the density of branch points and the density of end points in a skeleton representing the blood vessels and a fractal dimension for the skeleton.

U.S. Patent Application Publication No. 2007/0287897 to Faris, Gregory, incorporated herein by reference, discloses an in vivo optical imaging system and method of identifying unusual vasculature associated with the angiogenic vasculature in tumors. An imaging system acquires images through the breast. Benign, noninvasive oxygen and carbon dioxide are used as vasoactive agents and administered by inhalation to stimulate vascular changes. Images taken before and during inhalation are subtracted. An optical vascular functional imaging system monitors abnormal vasculature through optical measurements on oxy- and deoxy-hemoglobin during inhalation of varying levels of oxygen and carbon dioxide.

U.S. Patent Application Publication No. 2007/0019846 to Bullitt, Elizabeth et al., incorporated herein by reference, discloses systems, methods, and computer program products for analysis of vessel attributes for diagnosis, disease staging, and surgical planning. A method for analyzing blood vessel attributes may include developing an atlas including statistical measures for at least one blood vessel attribute, which can be developed from blood vessel image data from different individuals. Blood vessel attribute measurements can be obtained from an individual subject and compared to the statistical measures in the atlas.

U.S. Pat. No. 7,074,188 to Nair et al., incorporated herein by reference, discloses a system and method for using backscattered data and known parameters to characterize vascular tissue. In one embodiment, an ultrasonic device is used to acquire radio frequency backscattered data—i.e. intravascular ultrasound ("IVUS") data—from a blood vessel to create an IVUS image using a computing device. The vessel is cross-sectioned to identify its tissue type and create a corresponding (histology) image. A region of interest, preferably corresponding to the identified tissue type, is identified on the histology image, and the computing device identifies a corresponding region on the IVUS image, after which the IVUS data that corresponds to the region of interest is identified. Signal processing is performed to identify at least one parameter, which is stored in a database along with the tissue type. In another embodiment, the characterization application is adapted to receive IVUS data, determine parameters related thereto, and use the parameters stored in the database to identify a tissue type.

U.S. Pat. No. 6,351,663 to Flower et al., incorporated herein by reference, discloses methods (i) for enhancing the clarity of fluorescent dye angiograms using relatively high dye concentrations; (ii) for determining the direction of blood flow within a blood vessel using fluorescent dye angiograms; (iii) of identifying blood vessels that feed a lesion, such as a choroidal neovascularization or tumor; and (iv) of reducing the flow of blood into lesions incorporating dye-enhanced photocoagulation.

U.S. Pat. No. 6,236,886 to Cherepenin et al., incorporated herein by reference, discloses a method of obtaining tomographic images of the human body and also discloses electrical impedance tomography, in which a source of electric current is used to send electric current at levels undetectable by a human being to pairs of electrodes, between which at least two electrodes are placed. An algorithm of image reconstruction makes it possible to obtain the distribution of absolute conductivity of a body, characterizing the state of soft and bone tissues and blood vessels.

U.S. Pat. No. 6,221,623 to Smith-McCune et al., incorporated herein by reference, discloses biochemical methods for detecting cervical dysplasia. Primary screening is effected by measuring a biochemical marker of apoptosis and/or angiogenesis in each of a population of cells derived from convenient, superficial swabbing, scraping or lavage of superficial epithelial cells from the cervix, wherein the marker indicates the presence of cervical dysplasia in the sample, and scoring the results of the measuring step for cervical dysplasia—i.e., ascertaining whether or not the marker is present—in the patient in the absence of any cytological examination.

U.S. Pat. No. 6,135,965 to Tumer et al., incorporated herein by reference, discloses an apparatus and methods for spectroscopic detection of tissue abnormality, particularly precancerous cervical tissue, using neural networks to analyze in vivo measurements of fluorescence spectra.

U.S. Pat. No. 5,462,059 to Ferrara et al., incorporated herein by reference, discloses a method for assessing and displaying vasculature in a tissue mass using ultrasound and optimal velocity dependent data acquisition to differentiate between received signals from stationary tissue and received signals from slowly moving blood.

DISCLOSURE OF THE INVENTION

The presently preferred embodiment of the invention discloses a method for the detection of atypical vessels by applying a pre-processing stage for contrast enhancement, a segmentation stage to identify regions of interest, and a post-processing stage to determine the final region of interest. The pre-processing stage smoothes the image and suppresses high intensity components using a top hat filter; enhances the contrast of the image using a top hat and bottom hat filter; enhances the red component of the image; and then enhances the contrast of the red component of the image. The segmentation stage identifies regions of interest for atypical vessels by locating regions of maximum texture and maximum gradient information in the image and calculating the intersection of that information. The post-processing stage identifies and removes features that are unrelated to atypical vessels and further refines the image using known color, shape and size information on atypical vessels to create an output image with a final region of interest. This automated method of atypical vessel detection is especially useful for diagnostic purposes such as cancer detection, namely, cervical cancer detection.

BRIEF DESCRIPTION OF THE DRAWINGS

FIG. 1(a) shows wide hairpin like vessels; FIG. 1(b) shows waste thread vessels; FIG. 1(c) shows tendril-like vessels; FIG. 1(d) shows bizarre branching waste thread vessels; FIG. 1(e) shows corkscrew vessels; FIG. 1(f) shows irregular roof-like vessels; FIG. 1(g) shows tree-like vessels; FIG. 1(h) shows comma-shaped, or tadpole-like vessels; and FIG. 1(i) shows irregular branching vessels.

FIG. 4(a) original image; FIG. 4(b) smoothed image;

FIG. 4(c) contrast enhanced image; FIG. 4(d) red channel enhanced image; and FIG. 4(e) contrast enhanced red channel image.

FIG. 6(a) high texture region; FIG 6(b) segmented texture region; FIG. 6(c) gradient detection; and FIG. 6(d) intersection of texture and gradient.

FIG. 8(a) cervix region; FIG. 8(b) cervical os region; FIG. 8(c) blood-like regions; FIG. 8(d) fold-like regions; FIG. 8(e) glandular lesion-like regions; and FIG. 8(f) region of interest for atypical vessels.

BEST MODE FOR CARRYING OUT THE INVENTION

Figure 1A:
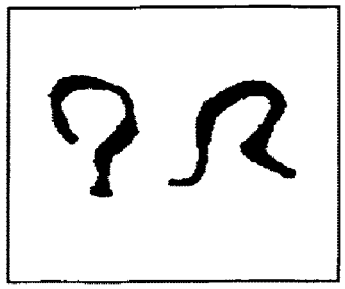
FIGS. 1(a)—FIG. 1(i) depict examples of atypical blood vessel shapes.
Figure 1B:
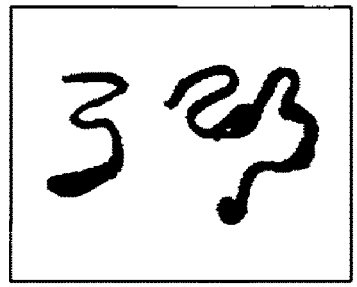
Figure 1C:
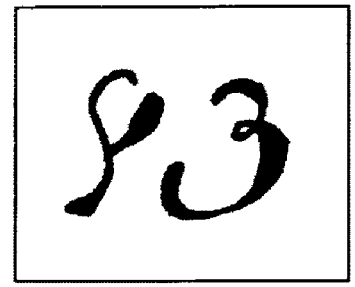
Figure 1D:
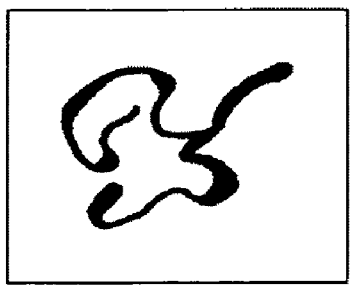
Figure 1E:
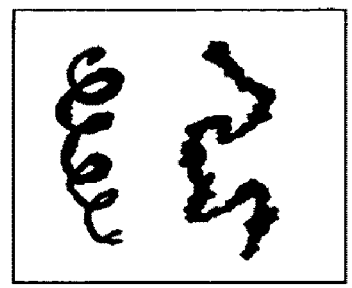
Figure 1F:
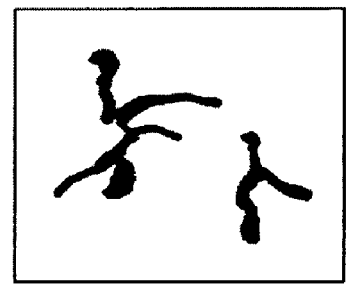
Figure 1G:
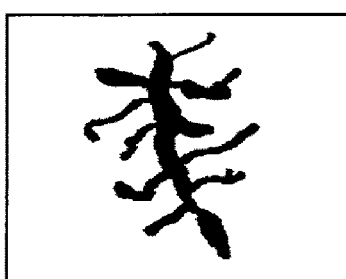
Figure 1H:
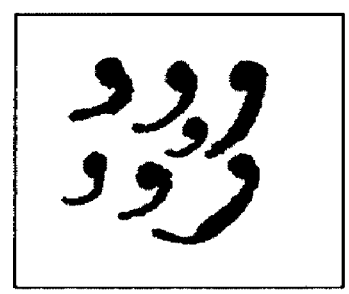
Figure 1I:
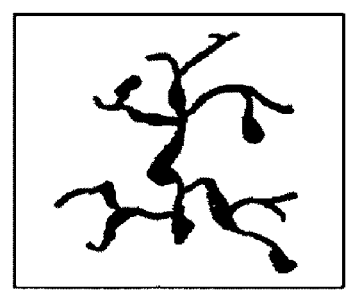
Figure 2:
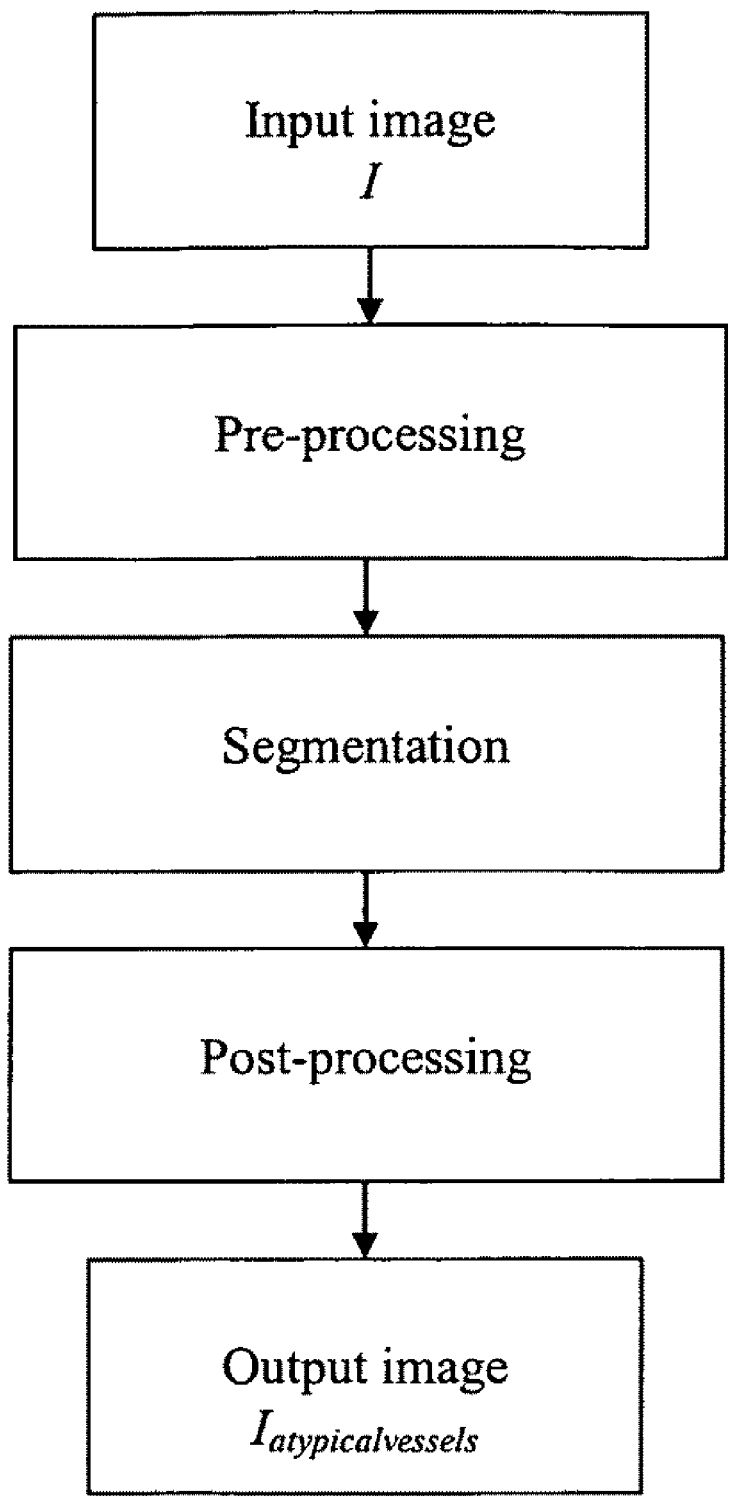
FIG. 2 shows a flowchart of the overall invention and atypical vessel detection process.

The presently preferred embodiment of the invention provides a systematic framework for the automated detection of atypical blood vessels in cervical imagery. A flowchart of the preferred embodiment of the invention is shown in FIG. 2. Due to the large variation of shapes, diameters, spacing and branching patterns of atypical vessels, a three-stage algorithm process is preferably implemented.

The atypical vessels detection of the presently preferred embodiment of the invention starts by collecting high-quality image data (digital images) of an organ (such as the cervix) in real-time during examination with a colposcope. A pre-processing stage is applied to the image data, which provides contrast enhancement of the original cervical image. The pre-processing stage conditions the image data for the segmentation stage by enhancing visualization of the vasculature in the image compared to the surrounding tissue. The second stage is the segmentation stage in which regions of interest (regions containing atypical vessels) are identified. In the segmentation stage, the texture and gradient characteristics of the atypical vessels are exploited to determine regions with a high likelihood of atypical vessels. In the final post-processing stage, false-positive detection of atypical blood vessels is minimized, if not completely eliminated. In the post-processing stage, other diagnostically significant features and regions are determined and removed from the region of interest resulting in a final image mask specifying the region for atypical vessels. The different stages of the presently preferred embodiment of the invention are described in more detail below.

Atypical Vessel Detection.

A. Atypical Vessel Pre-processing

The purpose of pre-processing is to enhance the contrast of regions with vascular patterns. In the presently preferred embodiment of the invention, we apply a series of steps based on mathematical morphology operations in order to enhance the contrast of vascular patterns compared to the surrounding tissue (J. Serra, *Image Analysis and Mathematical Morphology*, Academic Press, New York, 1982, incorporated herein by reference). Mathematical morphology is a technique for the analysis and processing of geometrical structures, such as blood vessel patterns. The basic idea in mathematical morphology is to use a structuring element to probe the structures in an image with a simple pre-defined shape, drawing conclusions on how this shape fits or misses the different structures in the image. The main structuring elements in mathematical morphology include shapes such as a disk, box, and diamond. The operators in mathematical morphology are commonly applied to digital images for edge detection, noise removal, image enhancement and image segmentation.

The preferred morphology operators used in the pre-processing stage are a combination of top-hat and bottom-hat filters (P. Soille, A note on morphological contrast enhancement, *Technical Report Ecole des Mines d'Alè's-EERIE* (1997), incorporated herein by reference; F. Meyer, Iterative image transformations for an automatic screening of cervical smears, The Journal of Histochemistry and Cytochemistry, *The Histochemical Society*, 128-135 (1979), incorporated herein by reference). The top-hat filter ("TH") captures high intensity (bright) areas in an image, whereas the output of the bottom-hat filter ("BH") defines the low intensity (darker) areas in the image, such as the blood vessel structures. Here, the top-hat filter is based on neighborhood ranking and uses the ranked value from two different sized areas. The brightest value in an area defined by a sliding window (preferably a disk shaped structuring element) is compared to the brightest value in a surrounding annular (ring-shaped) area. If the brightness difference exceeds a threshold value (typically defined as the average brightness of the surrounding area), the area is defined as a bright area. After the bright areas have been identified, a bottom-hat filter is preferably used to capture low intensity (dark) areas. Here, the size of the sliding window (preferably a disk shaped structuring element) is preferably chosen such that it slightly exceeds the diameter of the size of the vessel sought to be enhanced.

Figure 3:
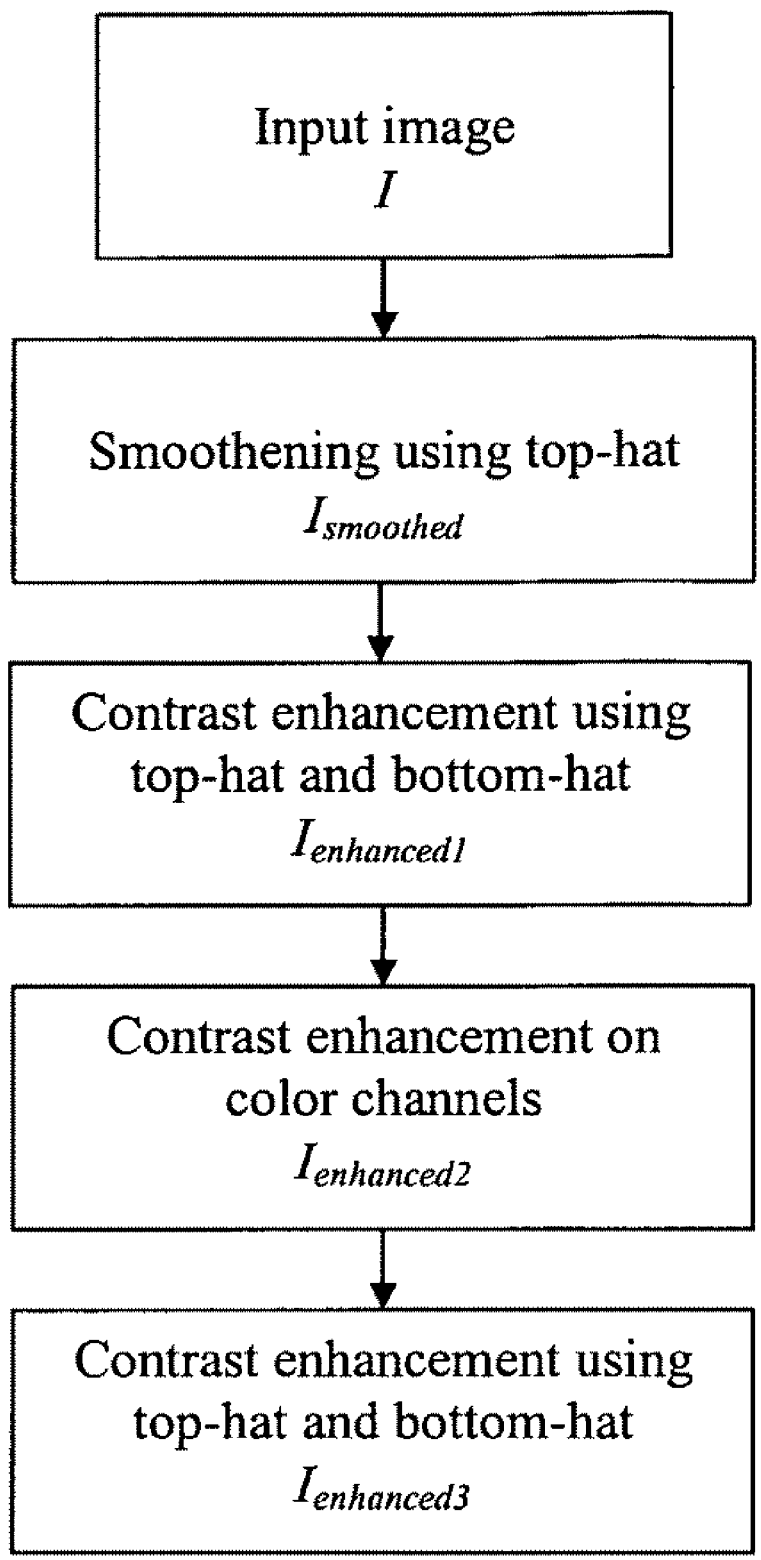
FIG. 3 shows the flowchart for atypical vessel pre-processing.
Figure 4:
FIG. 4(a)-FIG. 4(e) displays the results of image pre-processing.
Figure 4:
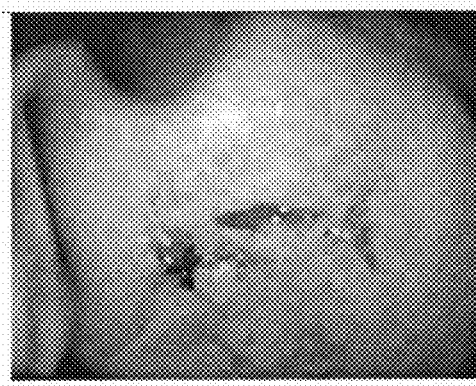
Figure 4:
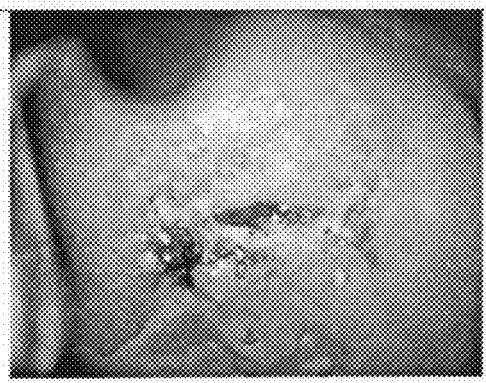
Figure 4:
Figure 4:

The pre-processing stage preferably starts with a color image of the cervix (designated I) and follows with four stages of morphology operations as illustrated by the flow chart in FIG. 3. The input image as illustrated in FIG. 4(a) is preferably first smoothed by subtracting the morphological top-hat of the input image (TH(I)) from itself, as illustrated by the following equation:

$$I_{smoothed} = I - TH(I) \quad (1)$$

This operation suppresses high-intensity (brightness) components (such as glare regions and saturated pixels) in the input image. The smoothed image is illustrated in FIG. 4(b).

The next step improves the contrast of the image by enhancing the contrast between vessel structures and the surrounding tissue. This involves the application of a contrast enhancement method based on starting with the smoothed image, adding (summing) the top-hat of the smoothed image, and subtracting the bottom-hat of the smoothed image to create a contrast enhanced image, as illustrated by the following equation:

$$I_{enhanced1} = I_{smoothed} + TH(I_{smoothed}) - BH(I_{smoothed}) \quad (2)$$

This method stretches the high-intensity (brightness) regions toward increased intensity whereas low-intensity regions are pulled towards decreased intensity, thereby increasing the contrast of the region by a greater amount than if only the low-intensity regions were subtracted (Wirth, M., Fraschini, M., and Lyon, J., Contrast enhancement of microcalcifications in mammograms using morphological enhancement and non-flat structuring elements, Proc. 17th IEEE Symposium on Computer-Based Medical Systems, (2008), incorporated herein by reference; K. Sun and N. Sang, Enhancement of vascular angiogram by multi-scale morphology, in *Bioinformatics and Biomedical Engineering*, 1311-1313 (2007), incorporated herein by reference). An example of the contrast enhanced image is displayed in FIG. 4(c).

Color images are often built of several stacked color components (color channels), each of them representing value levels of the given component (channel). For example, RGB images are composed of three independent components for red, green, and blue primary color components. The invention preferably achieves further contrast enhancement by augmenting the contrast of the red component through the addition of the green and blue component values of the contrast enhanced image ($I_{enhanced1}$) to create a red component enhanced image, as illustrated by the following equation:

$$I_{enhanced2} = I_{enhanced1}(\text{GreenChannel}) + I_{enhanced1}(\text{BlueChannel}) \quad (3)$$

This enhances the vascular patterns of the cervical image, as shown in FIG. 4(d). Green and blue channel values for vessel structures are low, and their values for background tissues are high. When the green and blue components are added to the contrast enhanced image enhanced $I_{enhanced1}$, colors corresponding to background tissue get closer to saturation while the vessel structure colors (corresponding to the red channel) do not change by much, thus adding more contrast to the vessel structures.

The final step of the pre-processing stage preferably involves again applying the contrast enhancement method of Equation (2) to the red component enhanced image, as illustrated by the following equation:

$$I_{enhanced3} = I_{enhanced2} + TH(I_{enhanced2}) - BH(I_{enhanced2}) \quad (4)$$

This step again stretches the high-intensity regions toward increased intensity and low-intensity regions towards decreased intensity, resulting in a contrast enhancement of the red component-enhanced image (a contrast enhanced red component image), as displayed in FIG. 4(e). In the next stage, the segmentation stage, the enhanced images of Equation (3) and (4) will be further evaluated for atypical vessel detection.

B. Atypical Vessel Segmentation.

Figure 5:
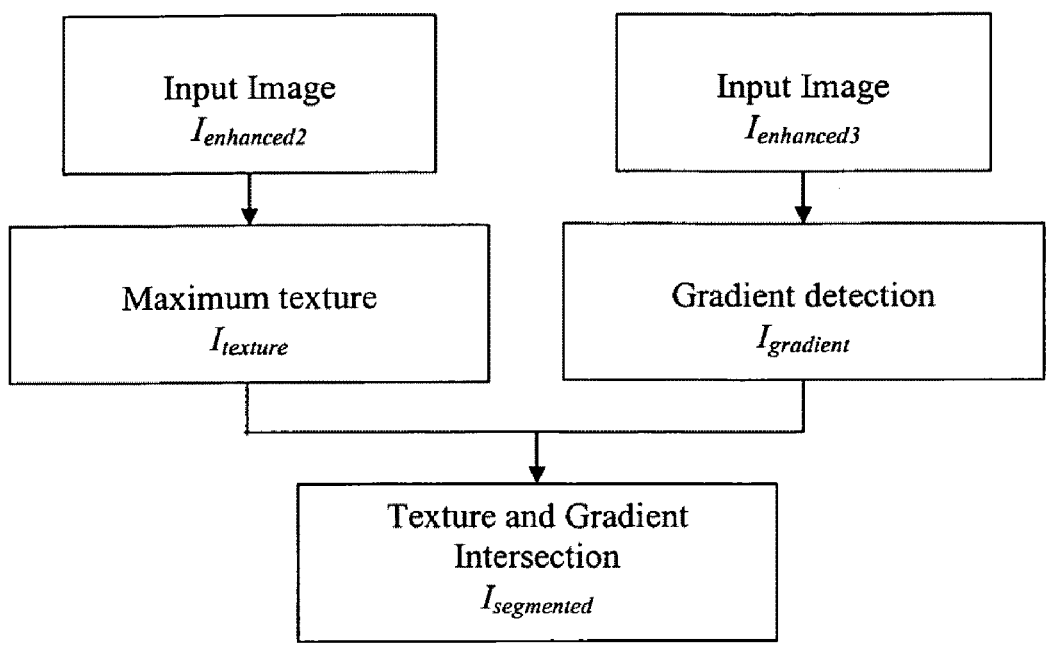
FIG. 5 shows the flowchart for atypical vessel segmentation.

The purpose of the segmentation stage is to identify regions of interest for atypical vessels. As atypical blood vessels typically are characterized by rich texture and high gradients (see below), a combination of texture and gradient algorithms is applied to identify the regions of interest for atypical vessels. The flowchart for the segmentation stage is displayed in FIG. 5.

Texture analysis refers to the characterization of regions in an image by their texture contents, and attempts to quantify qualities described in terms of rough, smooth, silky, or bumpy, as a function of the spatial intensity (brightness) variations in an image. Thus, roughness or bumpiness refers to the variations in intensity values, or gray levels (originating from gray levels in a black and white version of the image). For the cervix, a texture region is referred to as the region which is rich in texture content, i.e., has high intensity (brightness) variations.

Figure 6:
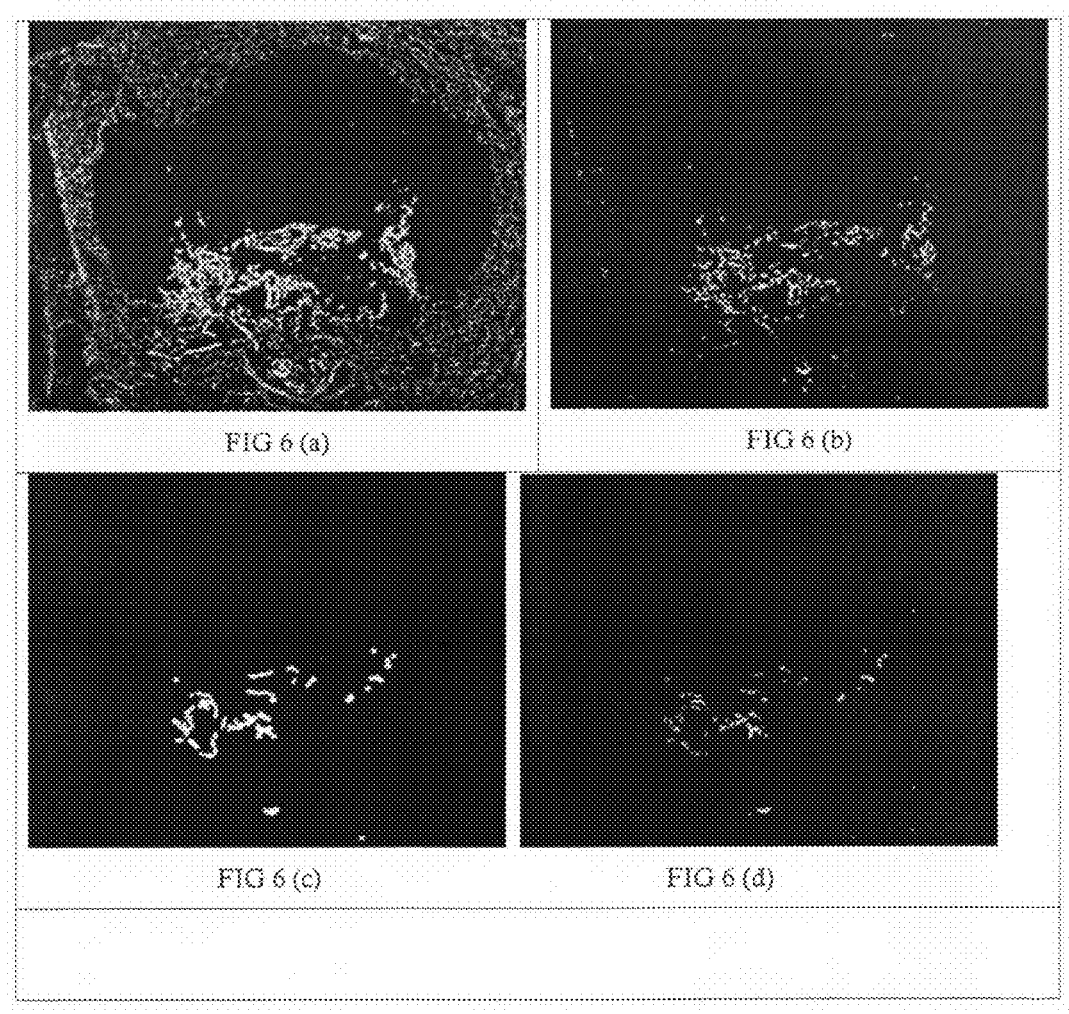
FIG. 6(a)-FIG. 6(d) display the results of the identification of regions of interest (segmentation) for atypical vessels.

A set of morphological filters is applied on the contrast-enhanced image of Equation (3) ($I_{enhanced2}$) (the red component enhanced image) in order to extract regions containing maximum texture. The bottom-hat filter is applied to the contrast-enhanced image using a line-shaped structuring element with different orientations of 0°, 45°, 90° and 180°. The length of the line-shaped structuring element is preferably set to ensure that all thin and thick vessels are identified preferably this length is set at approximately 5, but the invention is operable within the range of 3-10. The union of the four images obtained through the different orientations results in an image with maximum texture (or a maximum texture image), as illustrated in FIG. 6(a).

A region-based segmentation is then performed on the maximum texture image in order to extract vessel-like structures. Because the maximum texture image has high intensities in regions with prominent features, a histogram-based threshold method is applied to obtain a binary image—i.e., a digital image having only two possible values, typically black or white, for each pixel (the smallest piece of information in an image) that contains most of the large features. The threshold is chosen to maximize the number of true detections of atypical vessels. A high threshold will decrease the number of true-positives and a low threshold will result in the identification of a large number false-positives. The output image from the segmentation step is shown in FIG. 6(b).

Generally speaking, the gradient is the rate of graded ascent or descent of some physical property, such as the rate and direction of a temperature change. In image analysis, gradient usually refers to the study of the direction and magnitude of edges in an image. In the present invention it can be noted that atypical vessels are typically observed to be surrounded by sharp gradients, or edges. In order to restrict the previously determined texture region to areas with sharp gradients, an edge-based segmentation technique is preferably applied. Although the current invention preferably applies the Canny edge algorithm (Canny, J., *A Computational Approach To Edge Detection*, IEEE Trans. Pattern Analysis and Machine Intelligence, 8:679-714, 1986, incorporated herein by reference), other edge detection algorithms such as those of Sobel, Prewitt, Roberts, Laplacian or Gaussian can also be used. The Canny edge algorithm is preferred due to its multi-stage algorithm implementation, designed to detect a wide range of edges in various types of images.

The Canny edge algorithm is preferably applied on the contrast-enhanced image of Equation (4) ($I_{enhanced3}$) (the contrast enhanced red component image). The Canny method applies two thresholds to the gradient: a high threshold for low-edge sensitivity, and a low threshold for high-edge sensitivity. The gradient, or edge detection, of the present invention preferably starts with the low-sensitivity result, and then expands on the detected region by including connected-edge pixels from the high-sensitivity result. This approach helps to fill in gaps in the detected edges. In order to encapsulate the areas around the identified gradients, the edges are further enhanced with a disk-shaped structuring element (using mathematical morphology), and the contours in the image are filled using the flood fill algorithm which fills in areas surrounded by edges (it fills a connected region of a multi-dimensional array with a specified symbol). The output is an image with maximum gradient information (a maximum gradient image). An example image resulting from the gradient detection is shown in FIG. 6(c).

The final step in the segmentation stage combines the results from the texture and gradient detection steps. The intersection of the segmented maximum texture region and the maximum gradient region is calculated, and this intersection (regions with both maximum texture and maximum gradient) determines the regions of interest for atypical vessels. The regions of interest for atypical vessels after the segmentation stage are displayed in FIG. 6(d).

C. Atypical Vessel Post-processing

Figure 7:
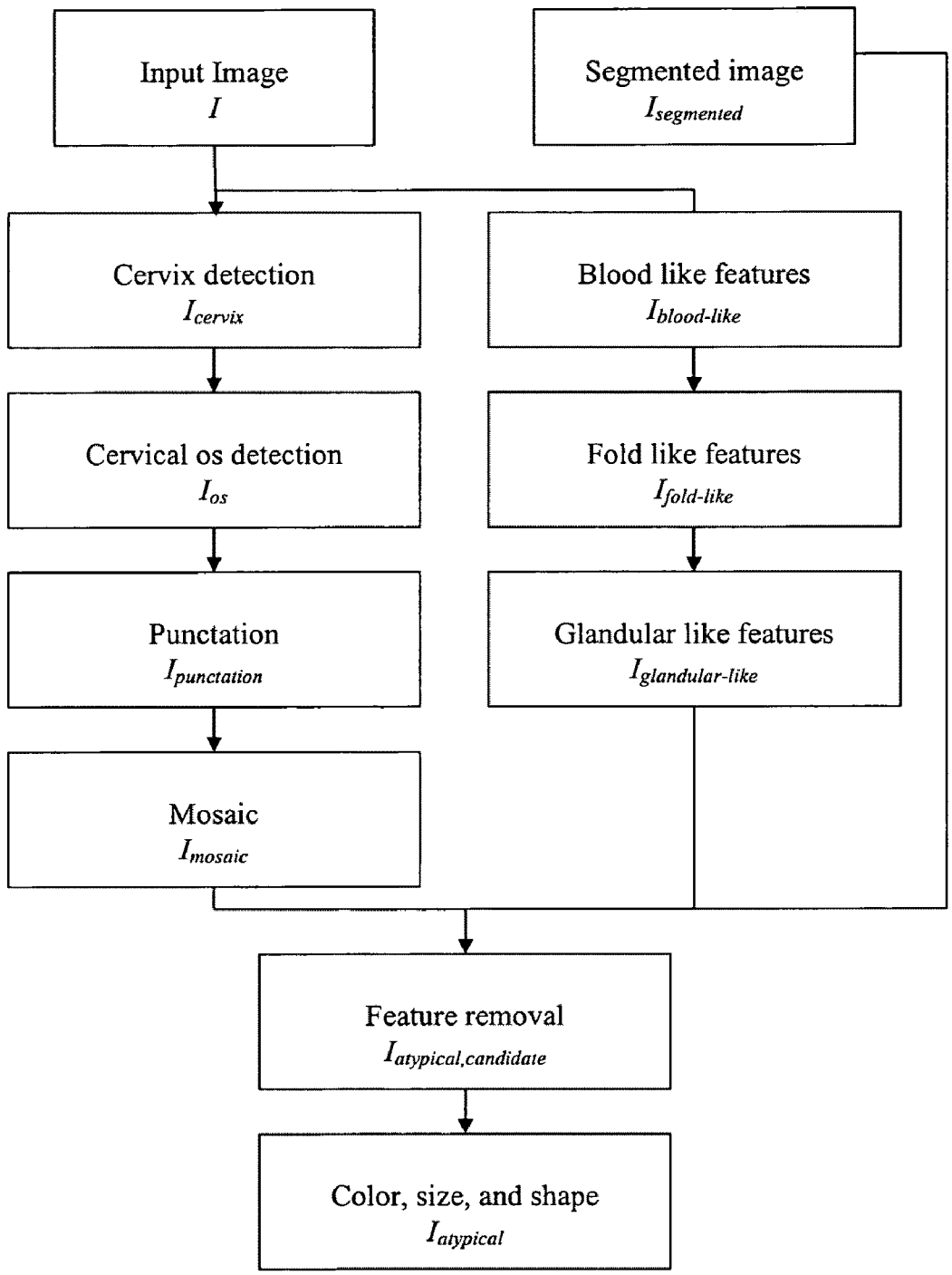
FIG. 7 shows the flowchart for atypical vessels post-processing.

The purpose of the post-processing stage is to eliminate false-positives of atypical vessels in the regions of interest previously obtained in the segmentation stage. This is accomplished by a two-stage process. First, identifying and removing clinically relevant features that are not attributed to atypical vessels (features unrelated to atypical vessels) in the cervical imagery; if these regions are overlapping with the regions of interest for atypical vessels, they are removed from the regions of interest. Second, color, shape, and size information from the regions of interest are used to further narrow the atypical vessel feature space. The flowchart of the post-processing stage is shown in FIG. 7.

Features unrelated to atypical vessels that should be excluded from the regions of interest include the regions that are not part of (i) the cervix, such as the vaginal wall and tools used during the colposcopic exam; (ii) the cervical os, or the external orifice of the uterus; (iii) the mosaic, or a plurality of non-overlapping images; (iv) punctation; or (v) blood-like, fold-like, and glandular lesion-like regions. The processes in which these features and regions are identified are described below.

Figure 8:
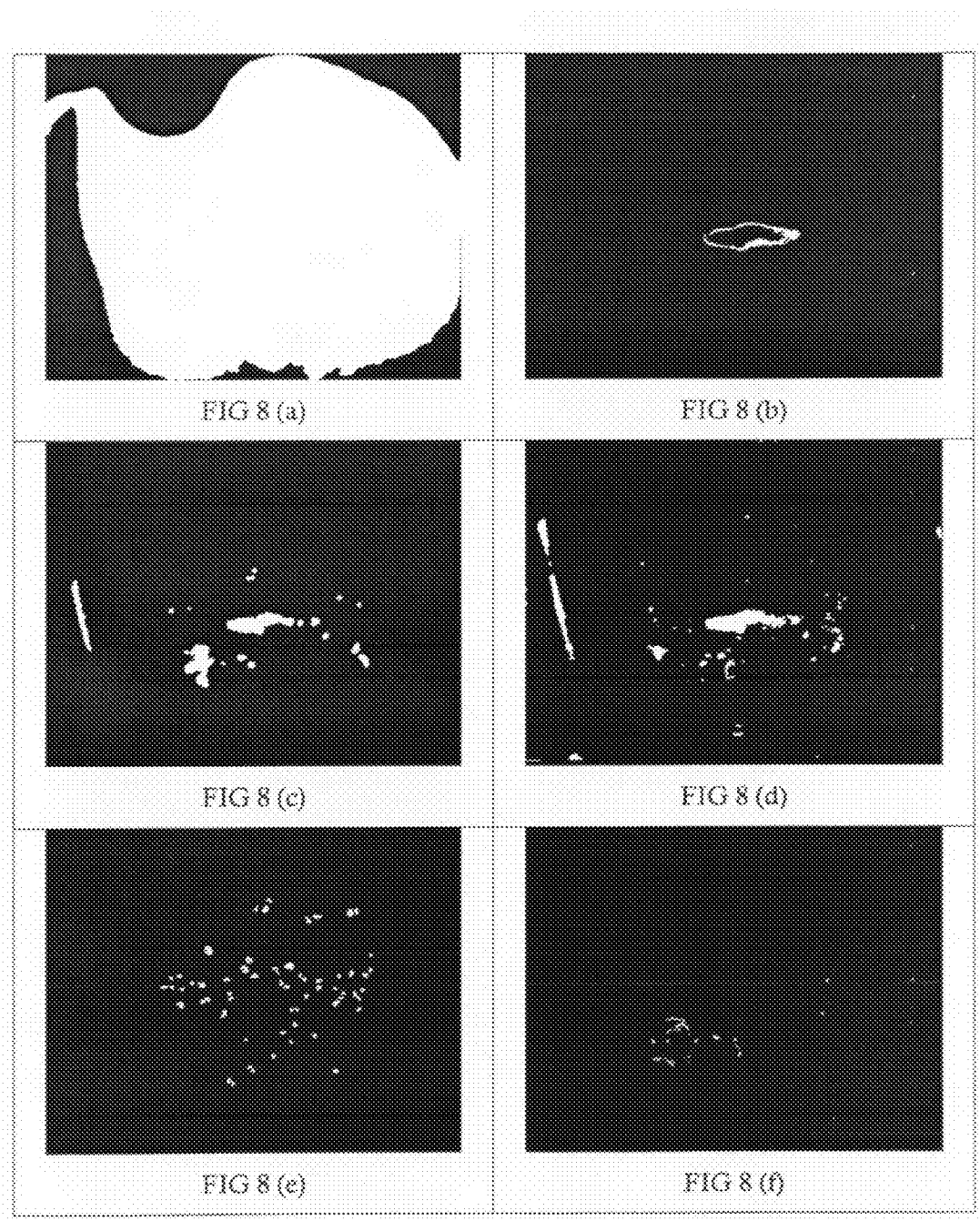
FIG. 8(a)-FIG. 8(f) displays the result of image feature post-processing.

The preferred cervix and cervical os region identification used in the present invention is based on the work presented by Li et al., which utilizes unsupervised clustering techniques to identify the cervix and the cervical os regions (W. Li, J. Gu, D. Ferris, and A. Poirson, Automated image analysis of uterine cervical images, *Proc. of SPIE* 6414, 65142P1-65142P9 (2007), incorporated herein by reference). Clustering refers to the classification of image attributes, including texture, shape and size, into different groups, or clusters, such that the data in each cluster share a common trait. FIGS. 8(*a*) and (*b*) show the cervix and cervical os region identified using the method described.

The preferred method in the detection of punctation and mosaic is also based on the work by Li et al., which applies mathematical morphology operations, branch point detection and vascular structure tracing, and gradient and shape information, to detect and outline regions with punctation and mosaic (W. Li and A. Poirson, Detection and characterization of abnormal vascular patterns in automated cervical image analysis, *Lecture Notes in Computer Science—Advances in Visual Computing* 4292, 627-636 (2006), incorporated herein by reference).

A number of regions are identified as regions of interest for atypical vessels during the segmentation stage due to the presence not only of blood streams and other blood-like textures on the cervix, but also of folds and crevices, and boundaries of glandular lesion-like features. Images with atypical vessels typically tend to have much more blood than others. The gradual flow of blood on the surface can be visualized as a thin stream and it can mimic vessels in size, shape and color sometimes. Also, areas where blood collects as a small pool in contours and ulcerations on the surface of the cervix look like pure blood and their shape and colors could sometimes mimic atypical vessels. In the current implementation of the invention, these regions are identified using combinations of morphology operations. As atypical vessels typically are thinner than blood-like features and blood streams, a blurring technique, referred to as "opposite contrast enhancement", is applied to the original image, as illustrated by the following equation:

$$I_{blurred}=I+BH(I)-TH(I) \quad (5)$$

Contrary to the contrast enhancement method applied in Equations (2) and (4), the method of Equation (5) compresses the entire image intensity by pulling the high-intensity regions toward decreased intensity, and low-intensity regions towards increased intensity, thereby decreasing, or blurring, the image. A bottom-hat operation is then applied on the green channel of the blurred image with different sized disk-shaped structuring elements. An Otsu-based gray-level threshold is then applied on the union of the different bottom-hat images, thereby creating an image mask representing features that resemble blood streams (N. Otsu, A Threshold Selection Method from Gray-Level Histograms, *IEEE Transactions on Systems, Man, and Cybernetics*, 9, 62-66 (1979)). A sample image resulting from the blood stream detection is shown in FIG. 8(*c*).

As folds display greater intensity variation than atypical vessels in the red image channel, the method described above for blood stream identification is used on the red channel of the image to create an image mask representing features that resemble fold-like regions. FIG. 8(*d*) displays the output from the fold detection algorithm.

In cervical imagery, glandular regions are small, dense, white-like structures that sometimes have distinctly marked red boundaries that mimic atypical vessels in color and size. In order to identify and eliminate these regions, Otsu's threshold method is applied on the red channel to obtain an image mask containing all the ridges in the red channel of the image. Next, a contrast-enhanced image of the green image channel is calculated using Equation (2), which provides an image with whitish regions that are possible candidates for glandular lesions. The image containing all the ridges in the red channel is then subtracted from the contrast-enhanced image of the green image channel. A binary mask for this image is created by using half the grayscale intensity as a threshold. In addition, based on phenomenology observations, very large (typically>5 mm in length) and very small (typically<0.1 mm in length) segments are removed. Additionally, segments with a mean blue value of less than half the maximum value, or segments with a solidity of less than 0.5, are also removed. Solidity refers to the state of the segment being solid, with 1 meaning completely solid, and 0 meaning not solid or completely scattered. It is calculated as a ratio between the area of the object of interest and the area of a convex envelope (the area of the smallest convex polygon that can contain the object) around the object of interest. The remaining structures in the binary image indicate glandular lesion-like objects. FIG. 8(*e*) illustrates the binary mask representing glandular lesion-like features.

All of the image masks from the previous step, comprising the detection of the cervix, cervical os, mosaic, punctation, and blood-like, fold-like, and glandular lesion-like regions, are combined with the output image from the segmentation step. Any segments from the maximum texture image obtained during the segmentation stage that are in contact with any of these image masks are removed. The remaining objects, or segments, are considered candidates for atypical vessel structures. This concludes the first step of the post-processing and FIG. 8(*f*) illustrates the output from this step.

The second and final, post-processing step uses known color, size and shape information for atypical vessels to further narrow the atypical vessel feature space to locate a final region of interest. Experimental studies on cervical imagery have shown that the color intensity of imaging pixels corresponding to atypical vessels typically has red channel values greater than 40% of the maximum intensity value of the sensor used, and green and blue values of less than 70% of maximum intensity value. In addition, if the red channel value of a pixel is less than that of its blue channel or, if the relative difference between the red and blue channels is less than approximately 10%, the pixel is not considered a part of the atypical vessel region.

Figure 9:
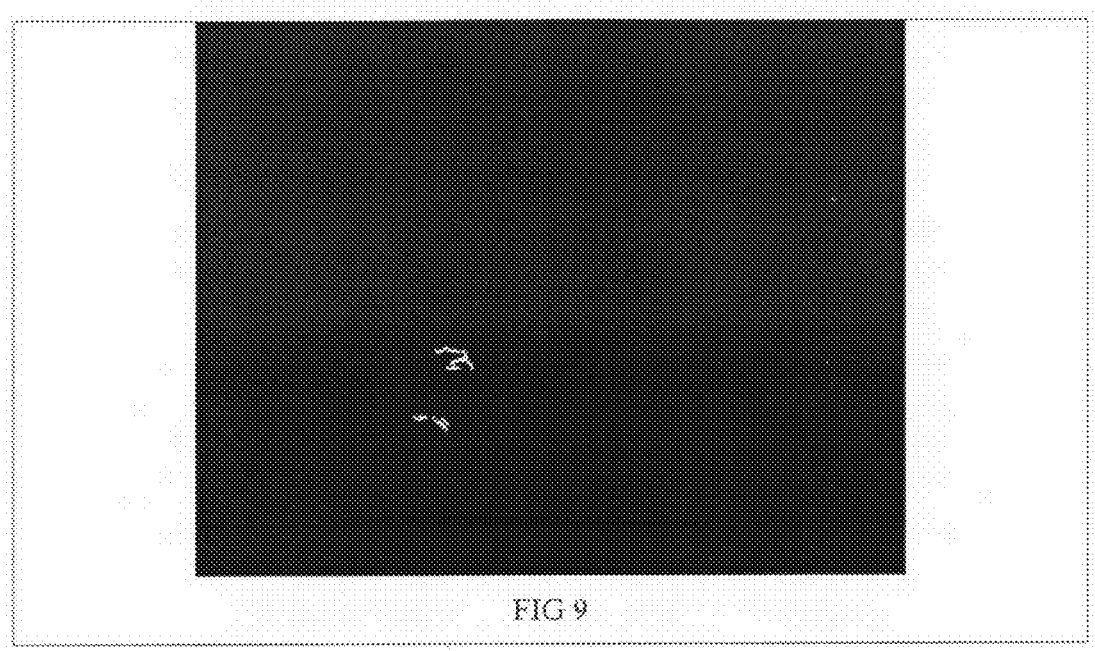
FIG. 9 displays the final result for atypical vessel detection after color, shape, and size information have been utilized.

A set of features is also used to characterize atypical vessels by their size and shape. Since the focus of the present invention is to extract prominent vessels indicative of pre-cancerous or cancerous lesions, an area threshold is applied in order to remove both very small and very large structures. If any structure (i) is less than 0.35 mm, or greater than 5 mm in length; or (ii) has an area greater than 0.01 mm$^2$, and a solidity greater than 0.8, or (iii) has an area between 0.004 mm$^2$ and 0.01 mm², a diameter of less than 0.18 mm, and a solidity greater than 0.7, that structure is eliminated as a candidate for an atypical vessel structure. FIG. 9 shows the final output image with atypical vessels detected by the method described in the current invention.

INDUSTRIAL APPLICATION

This invention provides possible extensions of atypical blood vessel detection and is not limited to the cervix. The method described may also be suitable for other tissue diagnosis instruments, as well as for those systems that require the detection of atypical vessels.

What is claimed is:

1. A method comprising:
    obtaining color images of the cervix wherein said images contain color components, atypical vessels, and features unrelated to atypical vessels;
    pre-processing to enhance contrast of said images to increase visualization of blood vessels from surrounding tissue creating a red component enhanced image and a contrast enhanced red component image, wherein said pre-processing comprises the steps of
    suppressing high intensity components by filtering an image from said images by a to hat filter, and subtracting the to hat-filtered image from said image to create a smoothed image;
    creating a contrast-enhanced image by
        filtering the smoothed image with a to hat filter,
        filtering the smoothed image with a bottom hat filter,
        adding the top hat-filtered smoothed image to, and subtracting the bottom hat-filtered smoothed image from said smoothed image;
    augmenting the red component of said contrast enhanced image to create said red component enhanced image;
    creating a contrast enhanced red component image by
        filtering the red component enhanced image with a to hat filter,
        filtering the red component enhanced image with a bottom hat filter,
        adding the top hat-filtered red component enhanced image to, and subtracting the bottom hat-filtered red component enhanced image from said red component enhanced image;
    segmenting said red component enhanced image and said contrast enhanced red component image to identify regions of interest, wherein said segmenting comprises the steps of
    applying a bottom-hat filter to said red component enhanced image to extract regions containing maximum texture;
    performing region-based segmentation on said regions containing maximum texture to create a maximum texture image;
    applying an edge detection algorithm to said contrast enhanced red component image to detect edges, and
    filling areas surrounded by said edges in said contrast enhanced red component image to create a maximum gradient image; and
    calculating the intersection of said maximum texture image and said maximum gradient image to locate said regions of interest;
    post-processing to eliminate false-positives of atypical vessels and determine a final region of interest from said regions of interest, wherein said post-processing comprises the steps of identifying and removing said features unrelated to atypical vessels in said regions of interest; and
    locating a final region of interest using known color, shape, and size information for said atypical vessels; and whereby said method detects said atypical blood vessels in digital images of tissue or organs for cancer diagnosis.

* * * * *